United States Patent
Zacks

(10) Patent No.: US 10,842,681 B2
(45) Date of Patent: Nov. 24, 2020

(54) COMPRESSION GARMENT

(71) Applicant: Jerome S. Zacks, New York, NY (US)

(72) Inventor: Jerome S. Zacks, New York, NY (US)

(*) Notice: Subject to any disclaimer, the term of this patent is extended or adjusted under 35 U.S.C. 154(b) by 535 days.

(21) Appl. No.: 15/365,309

(22) Filed: Nov. 30, 2016

(65) Prior Publication Data

US 2017/0151096 A1 Jun. 1, 2017

Related U.S. Application Data

(60) Provisional application No. 62/260,773, filed on Nov. 30, 2015.

(51) Int. Cl.
*A61F 13/00* (2006.01)
*A61F 13/08* (2006.01)

(52) U.S. Cl.
CPC ...... *A61F 13/085* (2013.01); *A61F 13/00008* (2013.01); *A61F 13/00063* (2013.01); *A61F 2013/0028* (2013.01)

(58) Field of Classification Search
CPC .............. A61F 13/085; A61F 13/00008; A61F 13/00063; A61F 2013/0028; A61F 13/00; A61F 2013/00093; A61F 2013/00119; A61F 5/00; A61F 5/01; A61F 5/0102; A61F 5/0127; A61F 5/0123; A61F 5/05858; A61F 5/05841; A61F 13/064; A61F 13/08; A41B 11/00; A41B 11/04; A41B 11/126; A41D 13/06; A41D 13/0543; A41D 13/065; A41D 13/08
USPC ............................................................ 602/63
See application file for complete search history.

(56) References Cited

U.S. PATENT DOCUMENTS

| | | | | |
|---|---|---|---|---|
| 835,980 | A * | 11/1906 | Paroubek | A61F 13/062 2/21 |
| 3,263,682 | A * | 8/1966 | Rosenfield | A61F 13/105 2/21 |
| 4,206,514 | A * | 6/1980 | Yamauchi | A41B 11/00 2/239 |
| 5,833,640 | A * | 11/1998 | Vazquez, Jr. | A61F 5/0111 602/27 |
| 5,934,599 | A * | 8/1999 | Hammerslag | A43C 1/00 242/396.1 |
| 6,289,558 | B1 | 9/2001 | Hammerslag | |
| 7,950,071 | B2 | 5/2011 | Jeong | |
| 2014/0259295 | A1* | 9/2014 | Guglielmo et al. | A43B 23/24 2/245 |

FOREIGN PATENT DOCUMENTS

WO WO2014159706 10/2014

* cited by examiner

*Primary Examiner* — Kim M Lewis
(74) *Attorney, Agent, or Firm* — McHale & Slavin, P.A.

(57) ABSTRACT

A closable compression garment comprises a first end, a second end, and a main body. The first end contains an opening sized and shaped to receive a lower extremity such as a foot, ankle, or leg within an interior portion. The main body contains a closure system which allows for the compression garment to traverse between a first insertion/removal position and a second closed position.

16 Claims, 12 Drawing Sheets

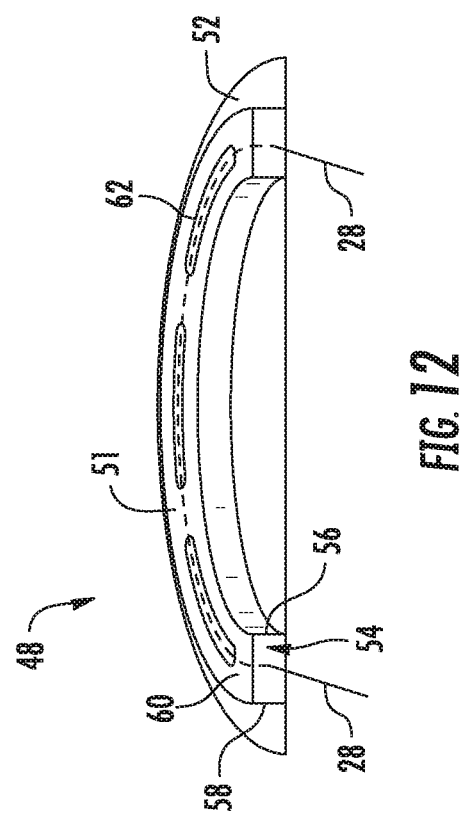
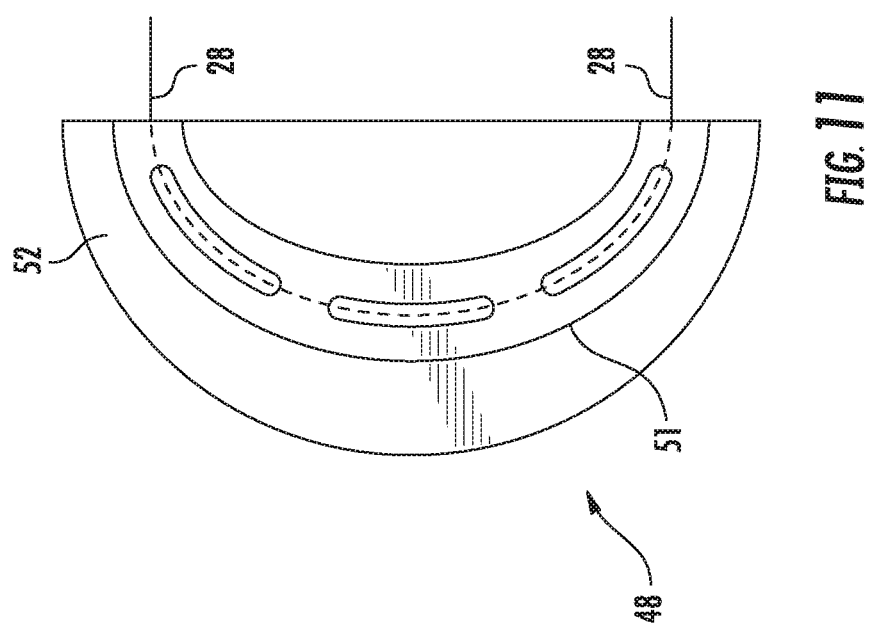

COMPRESSION GARMENT

CROSS REFERENCE TO RELATED APPLICATIONS

In accordance with 37 C.F.R. 1.76, a claim of priority is included in an Application Data Sheet filed concurrently herewith. Accordingly, the present invention claims priority to U.S. Provisional Patent Application No. 62/260,773, entitled "COMPRESSION GARMENT" filed Nov. 30, 2015. The contents of the above referenced application are incorporated herein by reference in its entirety.

FIELD OF THE INVENTION

The present invention is related to garments for use with a lower extremity such as a foot, ankle, or leg; to compression stockings or socks worn on a person's foot, ankle, or leg; and more particularly, to compression garments worn on a person's foot, ankle, or leg which utilize a closure system for ease in inserting or removing the compression garment.

BACKGROUND OF THE INVENTION

Compression garments have been used in many different settings. For example, the garments have been used in the sports arena to improve athletic performance. In the medical industry, compression garments have been used in various ways, such as to reduce edema and minimize the risk of embolism in individuals confined to a bed following surgery, or for individuals suffering from heart failure or chronic venous insufficiency (CVI). Regardless of the intended use, compression garments provide a benefit to individuals by improving venous blood flow from the foot and lower leg regions back to the heart. U.S. Pat. No. 7,950,071 describes a compression stocking that has many common features of the known compression stockings. The compression stocking described in the U.S. Pat. No. 7,950,071 includes a body that contains an opening for which a portion of the human body is inserted therein. While the compression stocking described in the patent teaches the use of various types of yarns as the inventive concept, the compression stocking is difficult to place onto the desired body part.

Therefore, what is needed in the art is a compression garment that is easy to place onto and remove from a body part.

SUMMARY OF THE INVENTION

The present invention describes a compression garment configured for easy application to or removal from a body part. In one embodiment, the present invention provides for a compression garment for applying compressive forces to a human body part comprising a flexible body configured for placement on a human body having a first end, a second end, and made of a material that applies a compressive force to the human body when placed thereupon. The flexible body comprises a longitudinal opening extending away from said first end towards said second end and forming a first flexible body longitudinal end and a second flexible body longitudinal end. The compression garment also includes a closure assembly configured to secure at least a first portion of the flexible body towards at least a second portion of said flexible body. The compression garment closure assembly may comprise at least one lacing member, a control unit for manipulating and controlling the at least one lacing, and at least one guide member sized and shaped to receive and support said at least one lacing member. The compression garment closure assembly is configured to place tension on the at least one lacing member, wherein tension applied to the at least one lacing member draws the first flexible body longitudinal end and said second flexible body longitudinal end together.

The present invention may also include a medical stocking for applying compressive forces to a human body part comprising a compression material configured for placement on a human body having a first open end, a second end, and a main body therebetween, the main body comprising a longitudinal opening extending from said first open end towards said second end and forming separable a first flexible body longitudinal end and a second flexible body longitudinal end; and a closure assembly configured to secure at least a first portion of the flexible body towards at least a second portion of the flexible body and comprising closure system. The medical stocking closure assembly is configured to place tension on the closure system, wherein tension applied to the at least one closure system draws the first flexible body longitudinal end and the second flexible body longitudinal end together.

Accordingly, it is an objective of the present invention to provide a compression garment having a closure system for easy insertion onto or removal from a leg, ankle, or foot.

It is a further objective of the instant invention to provide a compression garment having a closure system for easy insertion onto or removal from a leg, ankle, or foot which is traversable between an insertion/removal position and a closed position.

It is yet another objective of the instant invention to provide a compression stocking having a closure system for easy insertion onto or removal from a leg, ankle, or foot which is traversable between an insertion/removal position and a closed position.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 11 is a top view of an illustrative embodiment of the lace guide member;

FIG. 12 is a perspective view of the lace guide member shown in FIG. 11;

DETAILED DESCRIPTION OF THE INVENTION

Figure 1:
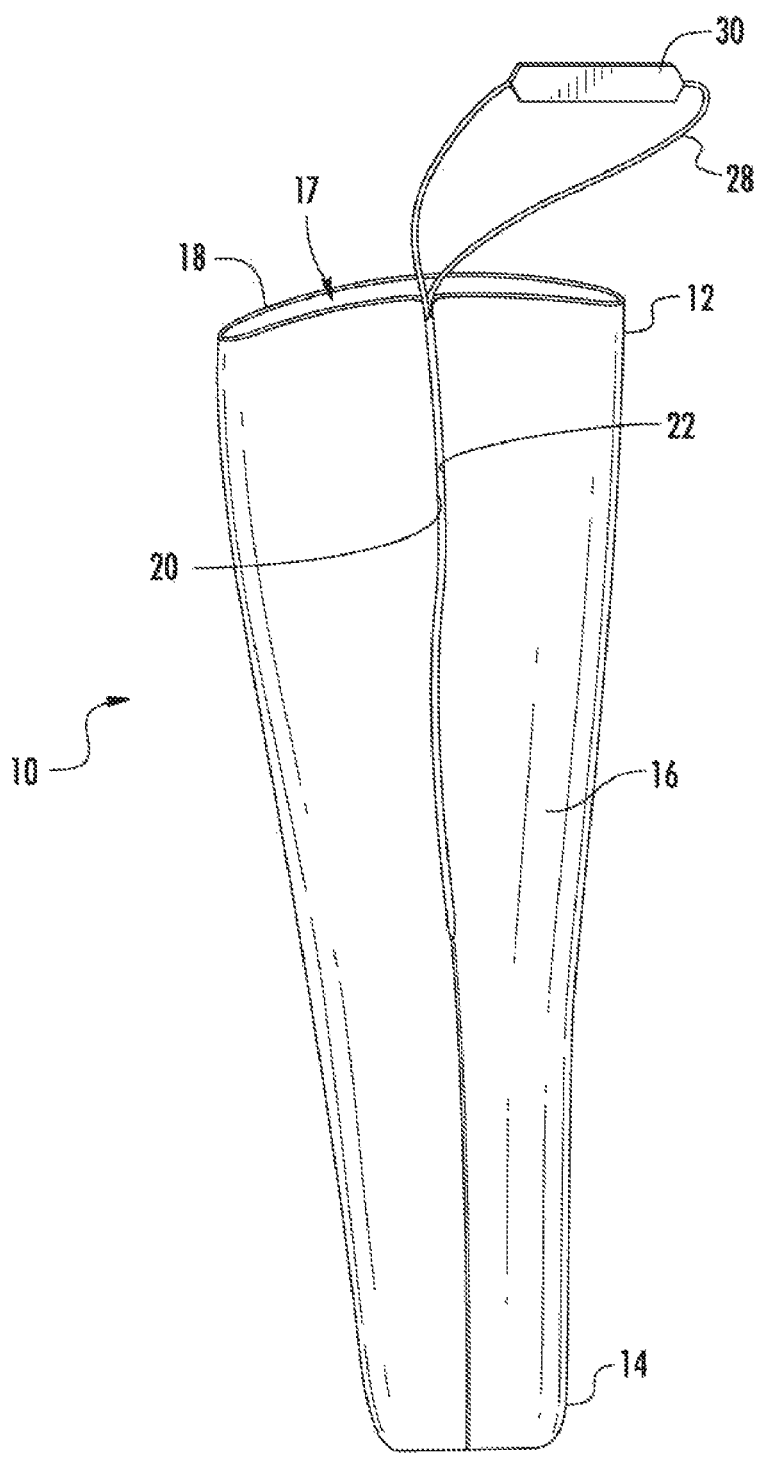
FIG. 1 is a front view of the compression stocking having a closure system, shown in the closed position.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIGS. 1-4, an illustrative embodiment of a compression garment having a closure system for easy insertion or removal, referred to generally as a closable compression stocking 10, is illustrated. The closable compression stocking 10 comprises a first end 12, a second end 14, and a main body 16 therebetween. The first end 12 contains an opening 18 sized and shaped to receive a lower extremity such as a foot, ankle, or leg within the interior portion 17. Notably, the closable compression stocking 10 may be configured to receive an individual's arm if needed. The second end 14 is shown as a closed end, but may be open if required. In the closed embodiment, the second end 14 may be shaped to mirror the contour or shape of a human foot and ankle.

Preferably, the closable compression stocking 10 is made of an elastic material so that the closable compression stocking 10 can expand to an expanded size when being placed on a person's ankle, foot, or leg, and return to its shape once removed from the body or resting on the ankle, foot, or leg. As such, the material used should be capable of being stretched repeatedly and still recover to near original shape and length once a tension is removed. In addition, the material may provide a pressure applied along the length of the compression stocking 10, thereby applying a compressive force to a human body portion when placed thereupon. As an illustrated example, the closable compression stocking 10 may be made of natural fibers such as cotton, wool, or rubber, or synthetic materials or fibers such as synthetic fabrics with a polymer base such as nylon (polyamide) or polyester, or elastane (spandex fibers, such as LYCRA, polyester-polyurethane copolymer), or mixtures of natural fibers and synthetic fibers. In addition to the elastic material, the closable compression stocking 10 may contain, or have embedded therein, anti-odor or anti-fungal materials. For example, the closable compression stocking material may be bonded with silver ions. Alternatively, the closable compression stocking material may be bonded with negatively and positively charged ions.

Figure 2:
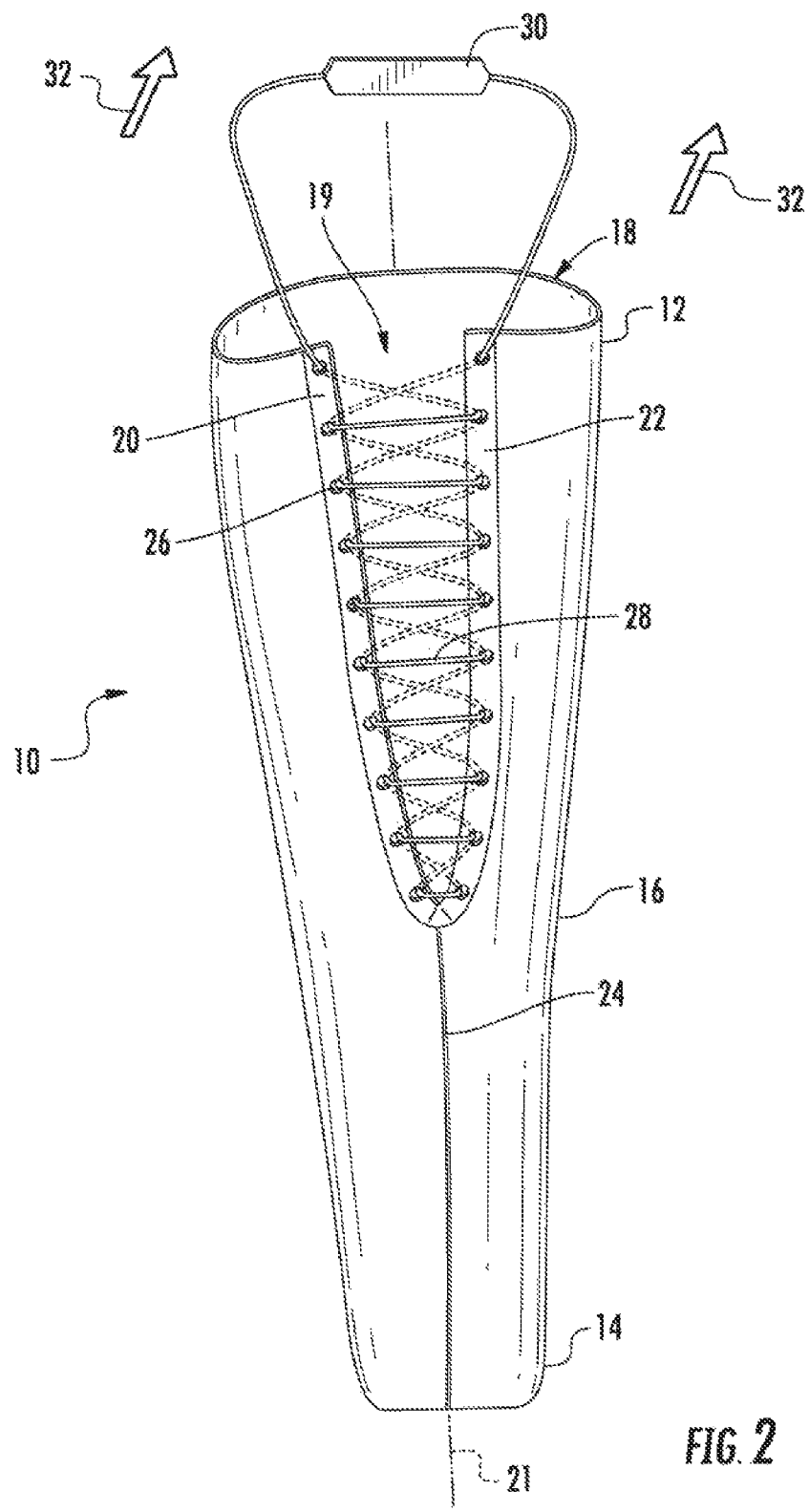
FIG. 2 is a front view of the compression stocking having a closure system, shown in the insertion/removal, or open position.
Figure 3:
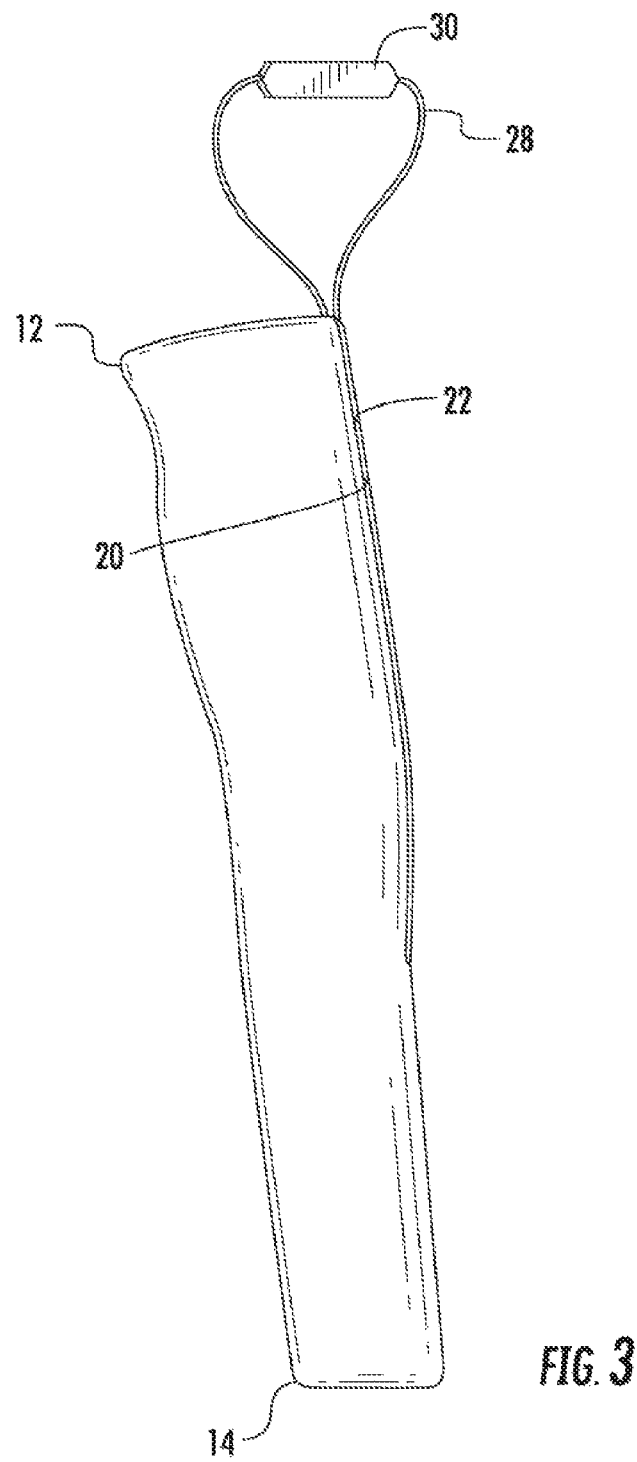
FIG. 3 is a side view of the compression stocking having a closure system, illustrating the closure system in the closed position.
Figure 4:
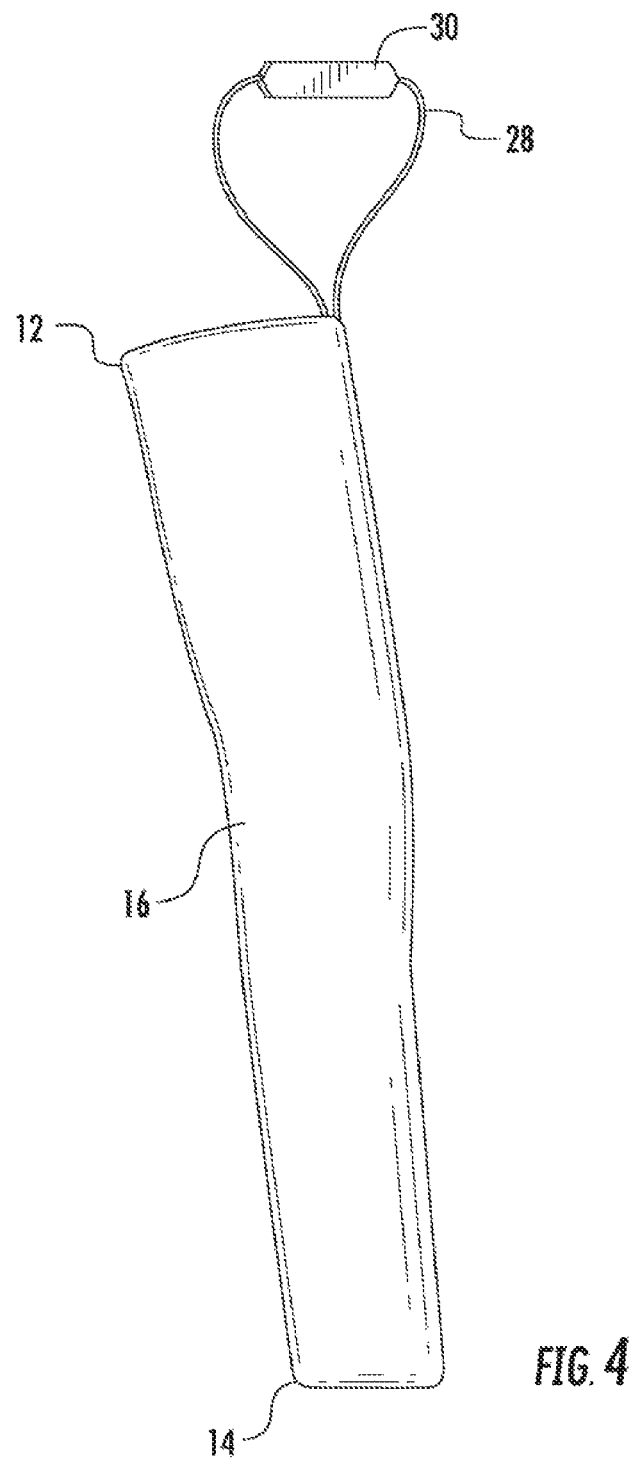
FIG. 4 is a side view of the compression stocking having a closure system, illustrating the side without the closure system.

The main body 16 of the closable compression stocking 10 contains a first opening 18 at the top portion and a second, longitudinal opening 19 defined by a distance between the main body ends 20 and 22, see FIG. 2. The longitudinal opening 19 runs along the longitudinal axis 21. The longitudinal opening 19 may be sized to run the entire length of the main body 16, i.e. from the first end 12 to the second end 14. As illustrated, the longitudinal opening 19 runs a partial distance from the first end 12 along the main body, ending at seam 24. The seam 24 extends to the opposing, second end 14. Located along each of the main body ends 20 and 22 are a plurality of eyelets or rings 26. Alternatively, rollers or miniature pulleys may be used. Each of the rings 26 supports, and may form part of, a closure system, illustrated herein as lacing 28. The lacing 28 interweaves within the rings 26 and extends out above the first end 12. A closure handle 30 allows a user to easily manipulate and control the lacing 28 by grabbing the closure handle 30 and applying a force in a direction away from the first end 12, see arrows 32. As the closure handle 30 is moved in the direction of arrows 32, the closable compression stocking 10 closes, see FIG. 1. Preferably, the lacing 28 is made of a material that does not create a restricted movement or has minimal frictional force with one or more portions of main body ends 20 and 22, so that when a force is applied the two ends move together as a single unit. The lacing 28 may be a monofilament (i.e. nylon, or a single form of plastic or co-polymer), fluorocarbon (i.e. a polyvinylidine fluoride or other thermoplastic fluoropolymer), braided fishing line, flexible steel, or steel alloy, coated flexible steel, or steel alloy, or any other material that does not create a restricted movement, has minimal frictional force, and has minimal or no memory.

Figure 5:
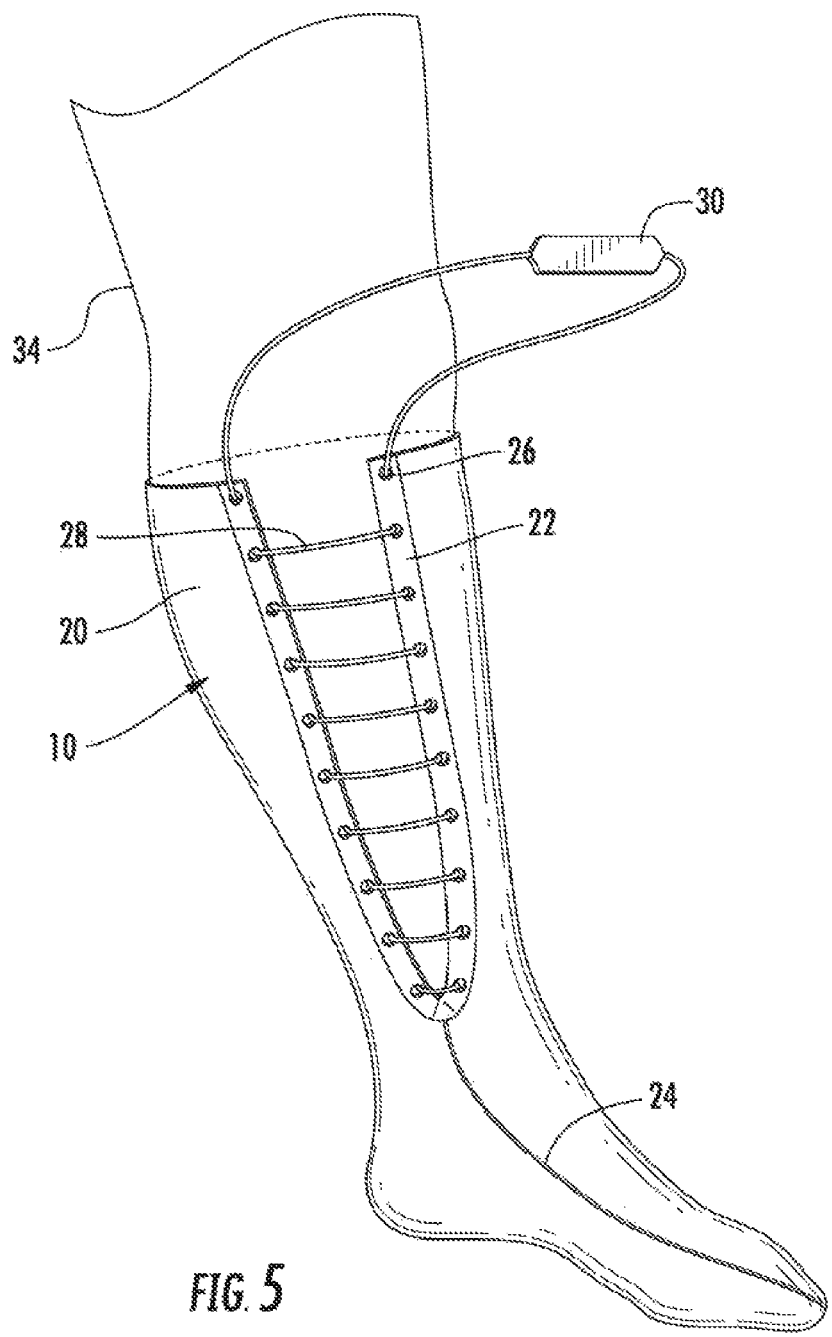
FIG. 5 is a perspective view of the compression stocking having a closure system placed on a leg and foot, shown in the insertion/removal position.
Figure 6:
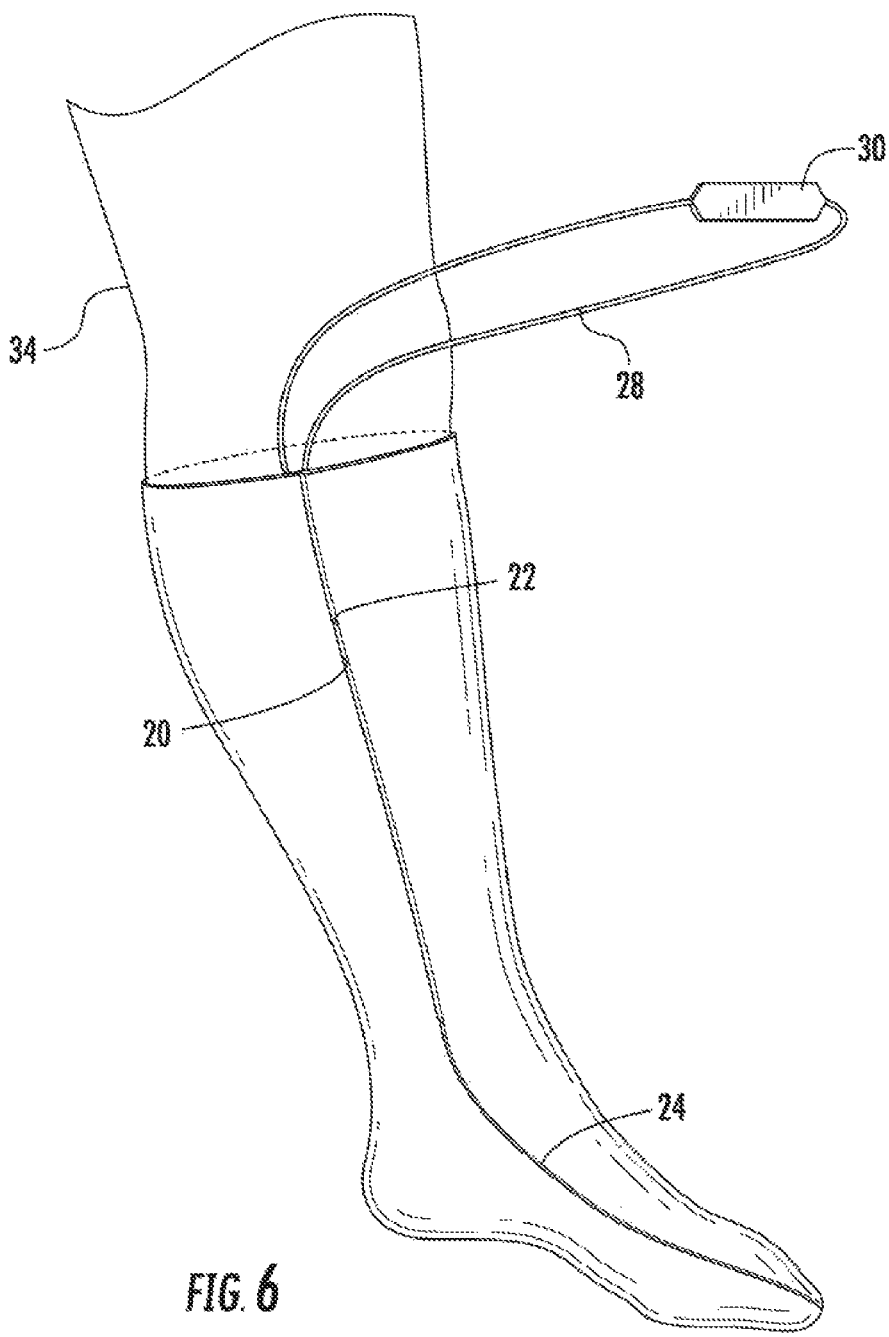
FIG. 6 is a perspective view of the compression stocking having a closure system placed on a leg and foot, shown in the closed position.

Referring to FIG. 5, the closable compression stocking 10 is shown placed on a leg 34, with the second end 14 covering the ankle and the foot. The main body ends 20 and 22 are spaced apart, providing a mechanism for the leg, ankle and foot to be inserted into the closable compression stocking 10. In this configuration, a user does not have to bunch or roll up the stocking in order to place on the leg. The lacing 28 is secured to the main body ends 20 and 22 through the rings 26. As the user pulls the closure handle 30 upwardly, or away from the leg 34, the lacing 28 forces the main body ends 20 and 22 to move towards each other in a manner that results in the two main body ends 20 and 22 coming together along the entire length having lacing. This action results in the closable compression stocking 10 being secured, in a closed position, to the foot 34, see FIG. 6.

Referring to FIGS. 7-10, the closable compression stocking 10 is shown with a closure system using a rotatable control unit. In this embodiment, tightening of the lacing 28 is controlled by a rotatable control unit 36. The control unit 36 contains a rotatable knob 38 supported by a support structure 40. A rotatable knob housing 42 receives and stores lacing 28. The lacing 28 enters into the knob housing 42 via openings 44 and 46. The rotatable knob housing 42 may also contain a ratchet system (not illustrated) or a tightening system using a rotatable spool, such as that described in U.S. Pat. No. 6,289,558, so, as the knob 38 is rotated, the tension on the lacing 28 is maintained. A release allows the tension applied to the lacing 28 to be removed and the lacing to be relaxed. Other locking mechanism, such as common cord locks used for venetian blinds, which often utilize wheels, pulleys, or gravity locks may be used to secure the lacing in a locked or unlocked position.

Figure 7:
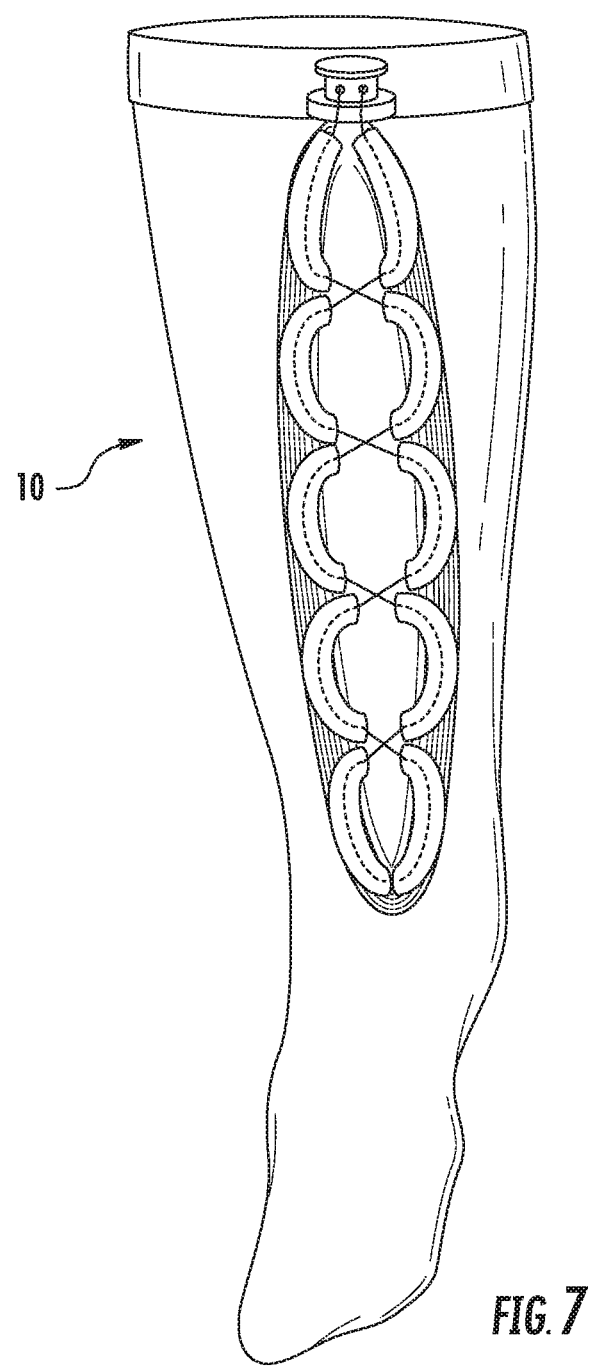
FIG. 7 is a front view of the compression stocking having a closure system having a rotatable control unit, shown in the open position.
Figure 8:
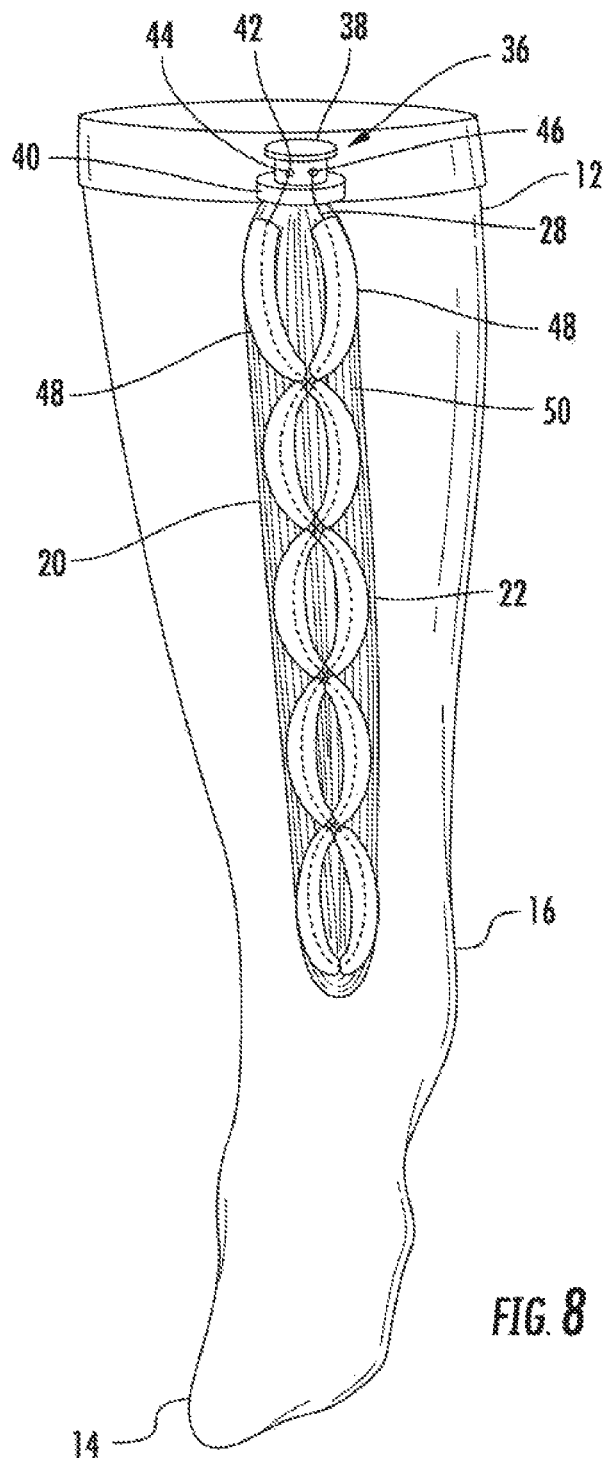
FIG. 8 is a front view of the compression stocking having a closure system having a rotatable control unit, shown in the closed position.
Figure 10:
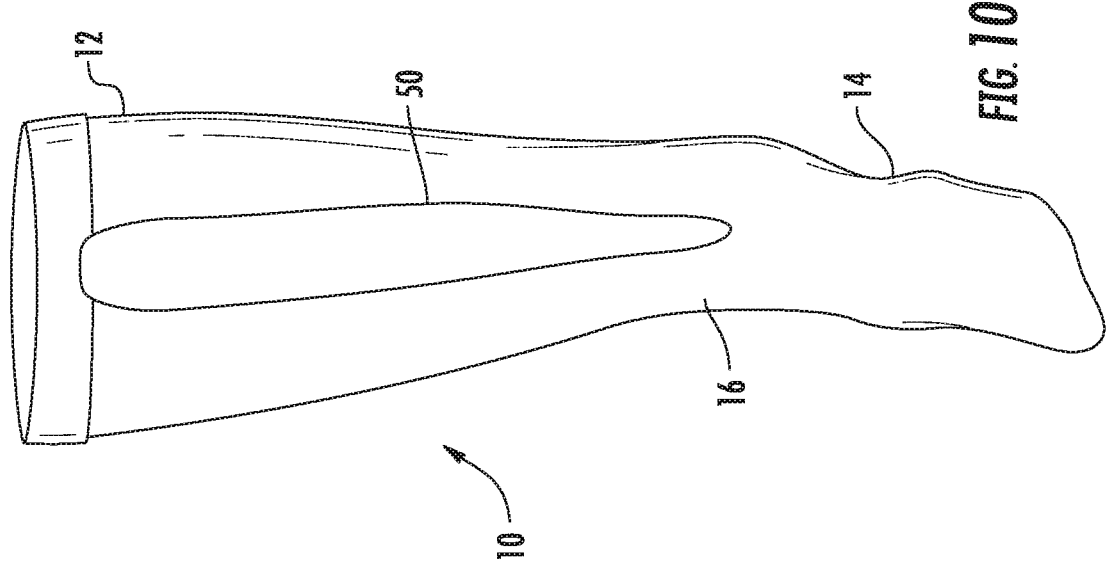
FIG. 10 illustrates the compression stocking having a closure system having a rotatable control unit shown inside out.
Figure 9:
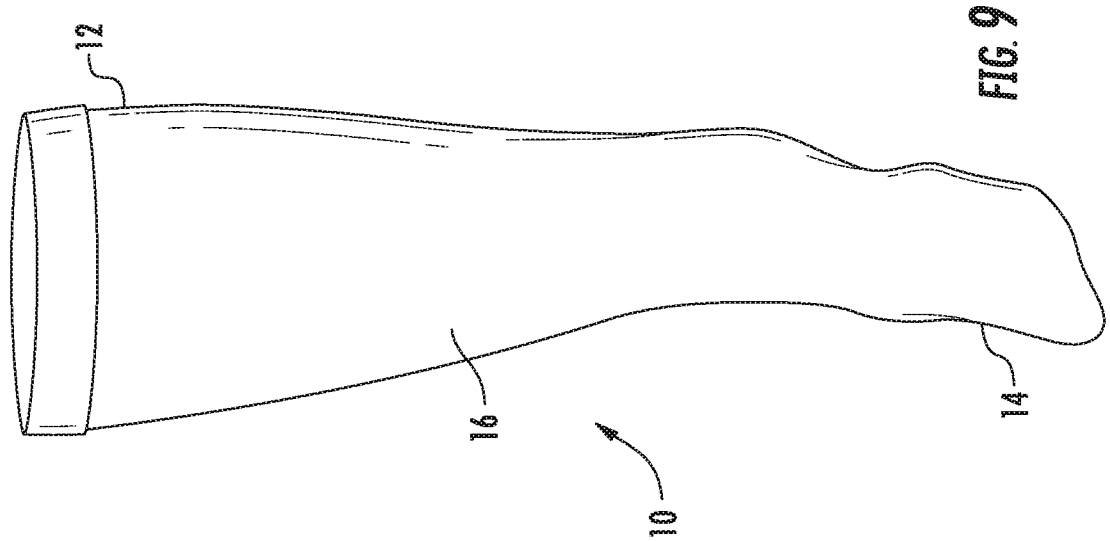
FIG. 9 is a side view of the compression stocking having a closure system having a rotatable control unit, illustrating the side without the closure system.

To aid in traversing the closable compression stocking 10 from an open, insertion position (see FIG. 7) to a closed position (see FIG. 8), a plurality of lace guide members 48 are coupled to the main body 16. The lace guide members 48 are configured to maintain the lace 28 in a proper orientation and position as the knob 38 is rotated. Each of the lace guide members 48 may be coupled directly to the main body 16. As shown in FIGS. 7 and 8, each of the lace guide members 48 are secured to an expandable cloth 50. The expandable cloth 50 is secured to, for example, the main body end 20 on one side and the main body end 22 at a second side via stitching. In this manner, the cloth 50 and main body 16 form a continuous surface (see FIG. 10, the closable compression stocking 10 shown inside out). An excess amount of cloth 50 may be used to allow the closable compression stocking 10 to close or open properly. The cloth 50 may be made of the same or different material as that of the main body 16.

FIGS. 11 and 12 provide illustrative embodiments of the lace guide members 48. A channel 51 is supported by a guide member support structure 52. Preferably, the guide member support structure 52 secures to the cloth 50 via a known coupling mechanism, such as through stitching or chemical fastening agents, i.e. glue. However, each of the lace guide members 48 may be coupled directly to the main body 16. The channel 51 contains an internal passageway 54 formed by side walls 56 and 58, top wall 60, and the support structure 52. The passageway 54 is sized and shaped to receive and hold lacing 28 therein. The top wall 60 may include a plurality of cut-outs 62.

Figure 13:
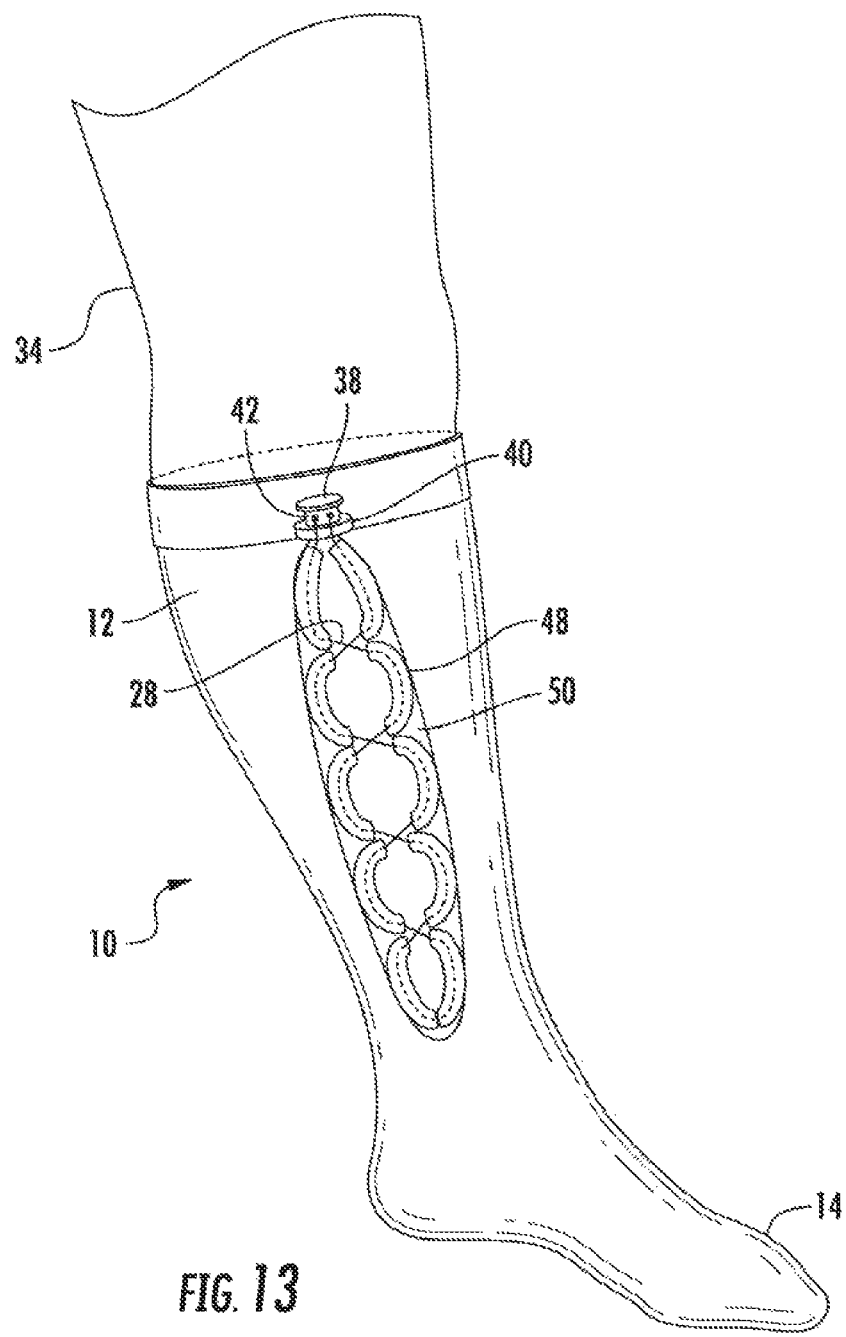
FIG. 13 is a perspective view of the compression stocking having a closure system having a rotatable control unit positioned on a leg and foot, shown in the insertion/removal position.
Figure 14:
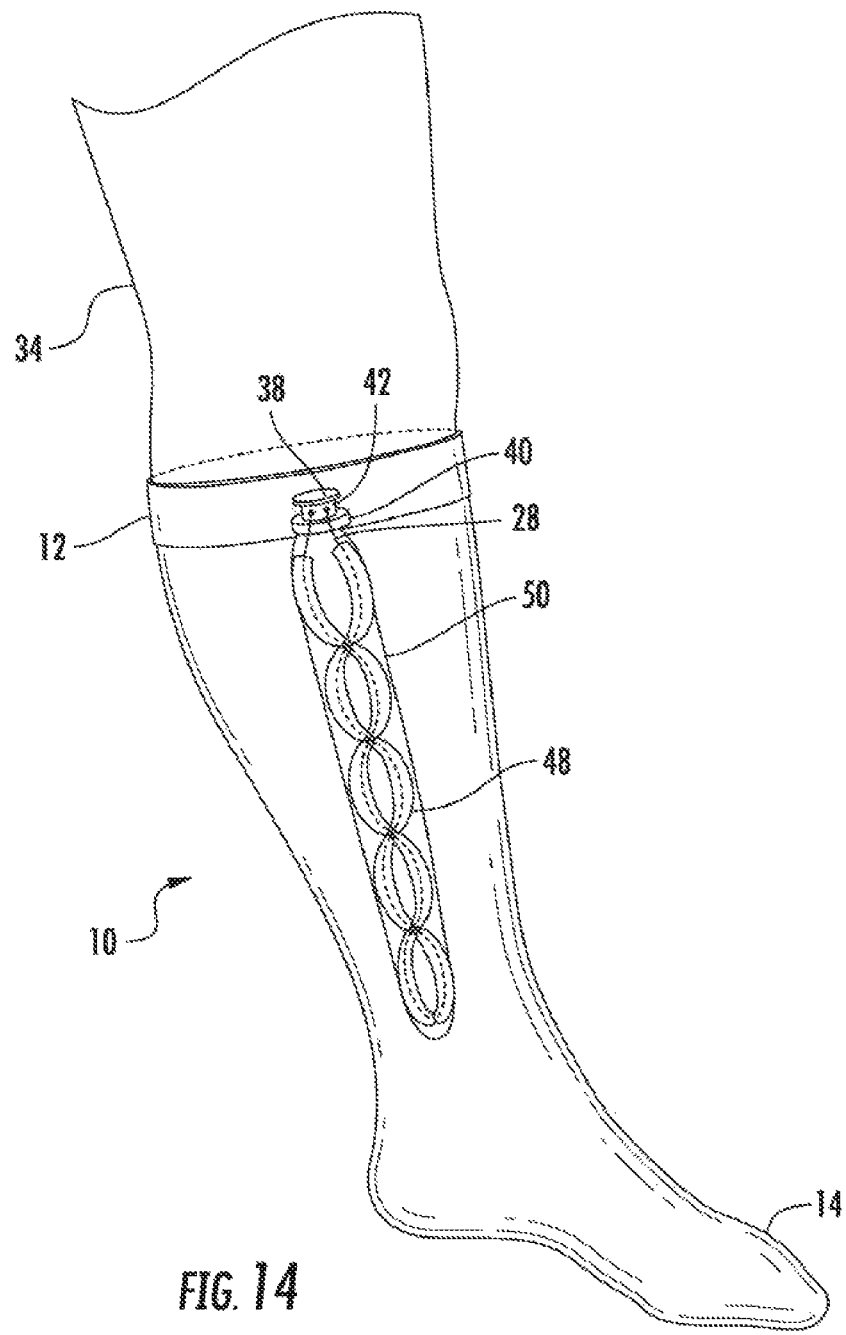
FIG. 14 is a perspective view of the compression stocking having a closure system having a rotatable control unit positioned on a leg and foot, shown in the closed position.

Referring to FIGS. 13 and 14, the compression stocking 10 with a closure system using a rotatable control unit is shown placed on a leg 34, with the second end 14 covering the ankle and the foot. The lace guide members 48 are spaced apart, providing a mechanism for the leg, ankle and foot to be inserted into the closable compression stocking 10. In this configuration, a user does not have to bunch or roll up the stocking in order to place on the leg. As the user rotates the rotatable knob 38, a tension is placed on the lacing 28. This action causes the lace guide members 48 to move inwardly towards the center of the main body 16.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A compression garment for applying compressive forces to a human body part comprising:
 a flexible body configured for placement on a human body having a first open end configured to receive at least a portion of a human body part, a second closed end having material configured to conform to a contour or shape of a human foot or ankle when said human foot or ankle is inserted therein, and made of a material that applies a compressive force to said human body when placed thereupon, said flexible body comprising a longitudinal opening extending away from said first open end towards said second closed end and terminating at said second closed end, said longitudinal opening forming a first flexible body longitudinal end and a second flexible body longitudinal end linked together by an expandable cloth;
 a closure assembly configured to secure at least a first portion of said flexible body towards at least a second portion of said flexible body comprising at least one lacing member;
 a control unit for manipulating and controlling said at least one lacing member; and at least one guide member sized and shaped to receive and support said at least one lacing member and to maintain said at least one lacing member in a predetermined orientation and position as said control unit is manipulated, said at least one guide member comprising a curved body having a first opening orientated along said longitudinal opening, a second opening orientated along said longitudinal opening, and an inner channel formed by two side walls, a bottom surface, and a top wall, said inner channel resting above said flexible body and sized and shaped to receive and hold said at least one lacing member and maintain said at least one lacing member in a position along an upper surface of said flexible body and said flexible body expandable cloth, said inner channel having a length which extends from said first opening of said curved body to said second opening of said curved body.

2. The compression garment according to claim 1 wherein said closure assembly comprises multiple guide members.

3. The compression garment according to claim 2 wherein said control unit is configured to place tension on said at least one lacing member, wherein tension applied to said at least one lacing member draws said first flexible body longitudinal end and said second flexible body longitudinal end together.

4. The compression garment according to claim 2 wherein said flexible body is configured to apply compression therapy to said human body part, said compression therapy comprising a pressure applied along a length of said flexible body.

5. The compression garment according to claim 2 wherein said flexible body second closed end is configured to be shaped to mirror a contour or shape of a human foot or ankle.

6. The compression garment according to claim 2 wherein said control unit for manipulating and controlling said at least one lacing comprises a ratcheting mechanism operatively connected to said at least one lacing.

7. The compression garment according to claim 2 wherein said flexible body comprises:
a first row of multiple curve shaped guide members; and
a second row of multiple curve shaped guide members,
wherein at least one end of one member of said first row curve shaped guide members is oriented to align with at least one end of one member of said second row curve shaped guide members, wherein said at least one lacing member is directed from or to said first row of multiple curve shaped guide members to or from said second row of multiple curve shaped guide members.

8. The compression garment according to claim 1 wherein said curved body of said at least one guide member comprises one or more cutouts in said top wall.

9. The compression garment according to claim 1 wherein said lacing is made of a material that does not create a restricted movement or has minimal frictional force with one or more portions of said flexible body so that when a force is applied, said first flexible body longitudinal end and said second flexible body longitudinal end move together as a single unit.

10. The compression garment according to claim 1 wherein said flexible body contains anti-odor or anti-fungal material.

11. The compression garment according to claim 10 wherein said anti-odor or anti-fungal material contains silver ions.

12. A medical stocking configured for applying compressive forces to a human body part comprising:
a compression material configured for placement on a human body having a first open end configured to receive at least a portion of a human body part, a second closed end having material configured to conform to a contour or shape of a human foot or ankle when said human foot or ankle is inserted therein, and a longitudinal opening extending from said first open end and terminating at said second closed end and forming separable a first longitudinal end and a second longitudinal end, said first longitudinal end linked to said second longitudinal end by an expandable material;
a closure assembly configured to secure at least a first portion of said flexible body towards at least a second portion of said flexible body and comprising lacing, a control unit, and a guide member sized and shaped to receive and support said lacing and to maintain said lacing in a predetermined orientation and position above an upper surface of said compression surface and said expandable material as said control unit is manipulated, said guide member comprising a curved body comprising a first opening, a second opening, and an inner channel formed by two side walls, a bottom surface, and a top wall, said inner channel sized and shaped to receive and hold said lacing, said inner channel having a length which extends from said first opening of said guide member curved body to said second opening of said guide member curved body.

13. The medical stocking configured for applying compressive forces to a human body part according to claim 12 wherein said control unit is configured to place tension on said lacing, wherein tension applied to said lacing draws said first longitudinal end and said second longitudinal end together.

14. The medical stocking configured for applying compressive forces to a human body part according to claim 12 wherein said lacing is made of a material that does not create a restricted movement or has minimal frictional force with one or more portions of said flexible body so that when a force is applied, said first flexible body longitudinal end and said second flexible body longitudinal end move together as a single unit.

15. The medical stocking configured for applying compressive forces to a human body part according to claim 12 wherein said control unit for manipulating and controlling said closure system comprises a ratcheting mechanism operatively connected to said lacing.

16. The compression garment according to claim 12 wherein said compression material comprises:
a first row of multiple curve shaped guide members; and
a second row of multiple curve shaped guide members,
wherein at least one end of one member of said first row curve shaped guide members is oriented to align with at least one end of one member of said second row curve shaped guide members, wherein said lacing is directed from or to said first row of multiple curve shaped guide members to or from said second row of multiple curve shaped guide members.

* * * * *